US007794669B2

(12) United States Patent
Gyonouchi et al.

(10) Patent No.: US 7,794,669 B2
(45) Date of Patent: Sep. 14, 2010

(54) CHEMICAL REACTION CARTRIDGE

(75) Inventors: Katsumori Gyonouchi, Musashino (JP); Takeo Tanaami, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 310 days.

(21) Appl. No.: 12/014,184

(22) Filed: Jan. 15, 2008

(65) Prior Publication Data

US 2008/0187469 A1 Aug. 7, 2008

(30) Foreign Application Priority Data

Jan. 17, 2007 (JP) ............................. 2007-007795

(51) Int. Cl.
*B01J 10/02* (2006.01)
*B01L 3/00* (2006.01)
*G01N 31/22* (2006.01)
*A61M 1/00* (2006.01)

(52) U.S. Cl. ........................... 422/129; 422/44; 422/46; 422/48; 422/58; 422/60; 422/102

(58) Field of Classification Search ................. 422/129, 422/102, 58, 60, 44, 46, 48
See application file for complete search history.

(56) References Cited

U.S. PATENT DOCUMENTS 3,036,894 A * 5/1962 Forestiere .................... 436/165
5,288,463 A * 2/1994 Chemelli ...................... 422/58
5,290,518 A * 3/1994 Johnson ........................ 422/58
6,426,230 B1 * 7/2002 Feistel ......................... 436/165
6,848,462 B2 2/2005 Covington et al.
7,056,475 B2 * 6/2006 Lum et al. .................. 422/100
2003/0025129 A1 * 2/2003 Hahn et al. ................. 257/200
2003/0143754 A1 * 7/2003 Lum et al. .................. 436/180
2004/0254559 A1 12/2004 Tanaami et al.
2005/0244308 A1 * 11/2005 Tanaami et al. ............. 422/180
2007/0077170 A1 * 4/2007 Tanaami et al. ............... 422/57
2008/0267827 A1 * 10/2008 Tanaami et al. ............... 422/99

FOREIGN PATENT DOCUMENTS

| | | | |
|---|---|---|---|
| DE | 299 03 296 | U1 | 8/2000 |
| DE | 10 2004 023 217 | A1 | 12/2004 |
| EP | 0 583 833 | A2 | 2/1994 |
| EP | 1 279 436 | A2 | 1/2003 |
| JP | 2005-37368 | A | 2/2005 |
| WO | WO 01/07982 | A1 | 2/2001 |

* cited by examiner

*Primary Examiner*—Walter D Griffin
*Assistant Examiner*—Huy-Tram Nguyen
(74) *Attorney, Agent, or Firm*—Sughrue Mion, PLLC

(57) ABSTRACT

Disclosed is a chemical reaction cartridge including a substrate which is a rigid body and an elastic body, and a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the substrate includes convex portions which protrude further than the elastic body at a surface of the substrate, on which the elastic body is formed.

11 Claims, 5 Drawing Sheets

CHEMICAL REACTION CARTRIDGE

BACKGROUND OF THE INVENTION

1. Field of the Invention

The present invention relates to a chemical reaction cartridge.

2. Description of Related Art

A chemical reaction cartridge which comprises an elastic body which has chambers and flow path formed inside and which enable the flowing and the blocking of the flow of the fluid inside the chambers and the flow path and a substrate of a rigid body to retain the position and the shape is suggested in JP2005-037368A for the purpose of safely and easily carrying out the synthesis, dissolution, detection, separation or the like of the solutions according to the determined protocol without individual differences in a low cost.

According to JP2005-037368A, the flowing and the blocking of the flow of the fluid is carried out by pressing the chambers and the flow path by deforming the elastic body by a roller or the like and by moving or stopping the roller or the like in the state where the chambers and the flow path are pressed.

A chemical reaction cartridge which has a convex portion formed on the surface of the elastic body right above the flow path and which tries to press the flow path surely even when the width, the shape and the number of the flow path change is disclosed in FIG. 8 and the paragraph 0024 of JP2005-037368A.

However, the above conventional techniques still have the following problems.

There is a case where the chemical reaction cartridge is placed on the desk or the like by the surface on which the elastic body is formed directing downward by a user. In such case, pressure to the elastic body occurs and there is a problem that the leakage or the unexpected flowing of the solution which is stored inside may occur. Particularly, in the chemical reaction cartridge in which the convex portion is formed on the surface of the elastic body right above the flow path, pressure to the flow path is concentrated. Therefore, the problem becomes clear. Further, concerning the chemical reaction cartridge which is formed with the elastic body on both sides of the substrate, it has to be placed by the surface which is formed with the elastic body directing downward.

SUMMARY OF THE INVENTION

In view of the above problem in the conventional technique, a main object of the present invention is to provide a chemical reaction cartridge having high safeness and high preservability which does not have a possibility of the leakage or the unexpected flowing of the solution which is stored inside occurring when the cartridge is placed regardless of either of the surfaces directing downward and which can be handled with ease.

According to a first aspect of the present invention, there is provided a chemical reaction cartridge comprising a substrate which is a rigid body and an elastic body, and a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the substrate includes convex portions which protrude further than the elastic body at a surface of the substrate, on which the elastic body is formed.

According to a second aspect of the present invention, there is provided a chemical reaction cartridge comprising a substrate which is a rigid body and an elastic body, and a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the elastic body includes a convex portion which protrude further than a portion of the elastic body in which the flow path or the chambers are formed at a surface of the substrate, on which the elastic body is formed.

BRIEF DESCRIPTION OF THE DRAWINGS

The above and other objects, advantages and features of the present invention will become more fully understood from the detailed description given hereinbelow and the appended drawings which are given by ways of illustration only, and thus are not intended as a definition of the limits of the present invention, and wherein.

DESCRIPTION OF THE PREFERRED EMBODIMENTS

Hereinafter, an embodiment of the present invention will be described with reference to the drawings. In the following, an embodiment of the present invention is disclosed and does not limit the present invention in any ways. The chemical reaction cartridge of the present invention is generally applied as a reactor which is also called "microreactor". The present invention is not limited to a specific usage.

Figure 1A:
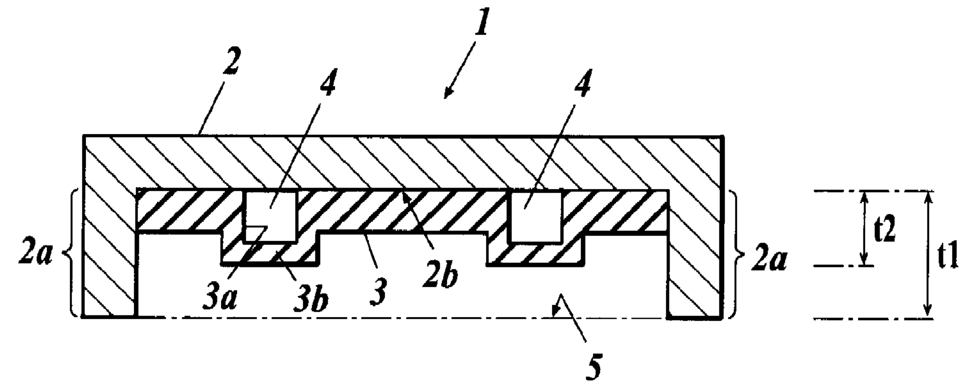
FIG. 1A is a cross sectional view of an example of a chemical reaction cartridge in which the present invention is implemented.

FIG. 1A shows a cross sectional view of an example of the chemical reaction cartridge in which the present invention is implemented.

As shown in FIG. 1A, a chemical reaction cartridge 1 comprises an elastic body 3 made of rubber having elasticity under air tight condition and a substrate 2 which is a rigid body made of hard material for determining the position and for maintaining the shape. The substrate 2 comprises convex portions **2*a*** at the edges.

As material for the elastic body 3, silicone rubber, PDMS (polydimethylsiloxane), natural rubber and a polymer thereof, acrylic rubber, polyurethane rubber or the like is used.

As material for the substrate 2, glass, metal, hard resin or a rigid body which can be bent is used.

As shown in FIG. 1A, concave portions 3*a* are formed on one surface of the elastic body 3. Flow path 4 and chambers are formed by attaching the portion of the surface of the elastic body 3, on which the concave portions 3*a* are formed excluding the concave portions 3*a* to the surface of the substrate 2. Two or more chambers are formed. The flow path 4 connects between the chambers and enables a substance to move between the chambers. The substance to be moved is a substance having flowability or liquid and other fluid substances. When the reactant to be moved is a substance which does not flow or a substance which is difficult to flow such as a solid substance or the like, a solution which includes the reactant is introduced into the chamber.

The moving of the substance is carried out as described below.

First, the pressing unit such as a roller, a squeegee, a syringe or the like is pressed onto the flow path 4 or onto the elastic body 3 above the chamber to press down the flow path 4 or the chamber. The inside substance can flow and move by pressing down the flow path 4 or the chamber. Further, the inside substance can flow and can be moved in the moving direction of the pressing position by moving the pressing position. Preferably, the moving of the pressing position is carried out by pressing the inner space until the space is sealed by allowing the inner walls of the flow path 4 or the chamber which face one another to contact at the pressing position.

The blocking of the flow of the substance is carried out by sealing the inner space by allowing the inner walls of the flow path 4 or the chamber which face one another to contact by the pressing unit. By using a plurality of pressing units, a substance can be moved by one of the pressing units, and at the same time, the substance can be prevented from moving further than the position of another pressing unit by pressing the flow path or the chamber by another pressing unit at a position forward than the substance in the moving direction.

The above described moving and blocking of the move is the basic operation, and the movement of the substance in the cartridge 1 is controlled in such way.

The chemical reaction cartridge 1 shown in FIG. 1A has convex portions 3*b* which are respectively formed on the surface of the elastic body 3 right above the flow path 4. In such cartridge 1, pressure can be concentrated at the flow path 4 and the moving of the substance and the blocking of the move of the substance can be carried out efficiently. Needless to say that this operation can be carried out even in the cartridge in which the surface of the elastic body 3 is flat, and does not have such convex portions 3*b*.

According to the above principle, the moving of the substance in the chemical reaction cartridge 1 is controlled and the operations for the chemical reaction are carried out.

For example, the chamber A, the chamber B, the chamber C and the flow path which connects with the chamber A and the chamber B and which join with the chamber C are formed in the cartridge, and the solution A introduced in the chamber A and the solution B introduced in the chamber B are mixed by moving the solution A and the solution B to the chamber C. Further, the cartridge can be used for react the solution C and the substance D with one another by sending the liquid mixture in the chamber C to the reaction chamber in which the substance D is fixed. There is a case where a waste liquid chamber is provided at the down stream of the reaction chamber to collect the waste liquid and air which are pushed out. It is also effective to make the flow path and the chambers placed relatively in down stream side in which the substance flows in be in a pressed condition by outside air pressure and the inside thereof is vacant.

The substrate 2 comprises convex portions 2*a* which protrude further than the elastic body 3 at the surface 2*b* of the substrate 2, on which the elastic body 3 is formed. That is, the surface 2*b* being the base line, the height t1 of the convex portions 2*a* are higher than the height t2 of the elastic body 3. The convex portions 2*a* are portions of the substrate 2 and are rigid bodies.

When the cartridge 1 is placed on the desk or the like by the protruding direction of the convex portions 2*a* directing downward, that is by the surface 2*b* directing downward as shown in FIG. 1A, the cartridge 1 is supported by the convex portions 2*a*. Therefore, the elastic body 3 will not be pushed by the placing surface 5 as long as the placing surface 5 is flat, and the unexpected leakage or flowing of the substance stored inside are prevented.

Figure 1B:
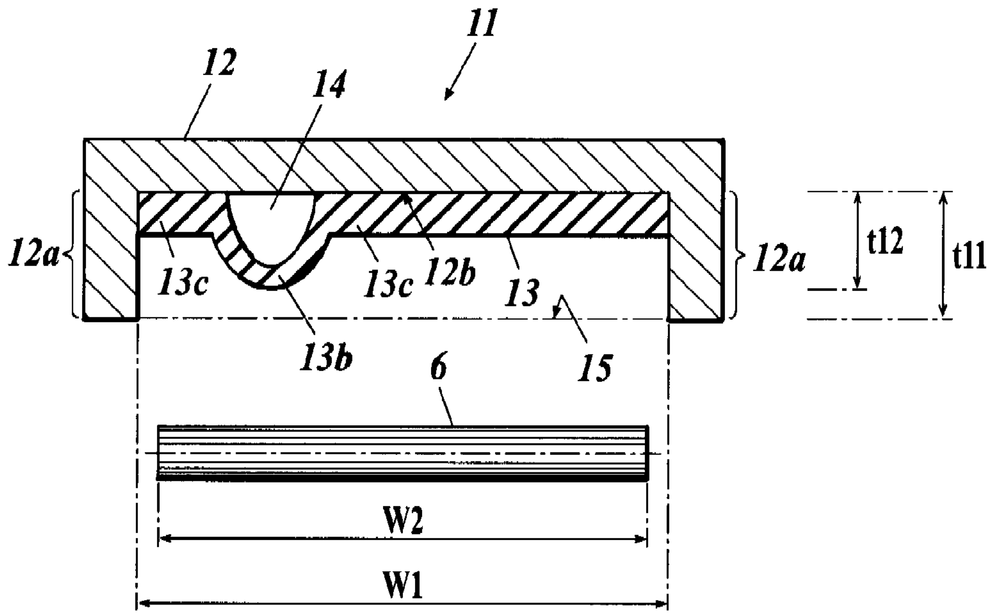
FIG. 1B is a cross sectional view of another example of the chemical reaction cartridge and a roller for pressing in which the present invention is implemented.

Another example of the chemical reaction cartridge 11 shown in FIG. 1B has a convex portion 13*b* formed on the surface of the elastic body 13 right above the flow path 14. The convex portion 13*b* is formed so as to be thinner than the portion 13*c* which is constructed by the surrounding elastic body 13, and the flow path is formed so as to be easily pressed down comparing to the chemical reaction cartridge 1 shown in FIG. 1A.

The substrate 12 comprises convex portions 12*a* which protrude further than the elastic body 13 at the surface 12*b* of the substrate 12, on which the elastic body 13 is formed. That is, when the surface 12*b* is the base line, the height t11 of the convex portions 12*a* is more than the height t12 of the elastic body 13. The convex portions 12*a* are portions of the substrate 12 and are rigid bodies.

When the cartridge 11 is placed on the desk or the like by the protruding direction of the convex portions 12*a* directing downward, that is by the surface 12*b* directing downward as shown in FIG. 1B, the cartridge 11 will be supported by the convex portions 12*a*. Therefore, the elastic body 13 will not be pushed by the placing surface 15 as long as the placing surface 15 is flat, and the unexpected leakage or flowing of the substance stored inside are prevented.

Figure 2A:
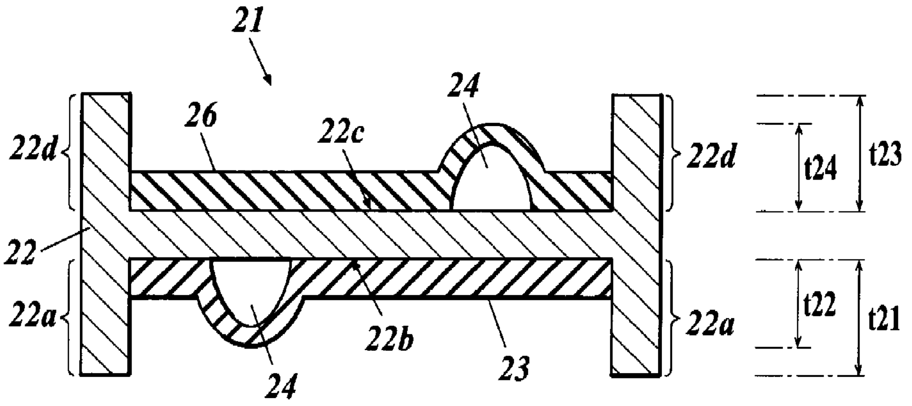
FIG. 2A is a cross sectional view of another example of the chemical reaction cartridge in which the present invention is implemented.

FIG. 2A shows an example of the cartridge in which the elastic body is formed on both surfaced of the substrate.

As shown in FIG. 2A, the substrate 22 of the chemical reaction cartridge 21 comprises the convex portions 22*a* and 22*b* which protrude further than the elastic bodies 23 and 26 on both the surface 22*b* of the substrate 22, on which the elastic body 23 is formed and the surface 22*c* of the substrate 22, on which the elastic body 26 is formed. That is, when the surface 22*b* is the baseline, the height t21 of the convex portions 22*a* is more than the height t22 of the elastic body 23. Similarly, when the surface 22*c* is the baseline, the height t23 of the convex portions 22*b* is more than the height t24 of the elastic body 26. The convex portions 22*a* and 22*d* are portions of the substrate 22 and are rigid bodies.

In such way, by applying the substrate 22 having the convex portions on both sides, similarly to the cases of the cartridge 1 and 11, the unexpected leakage or flowing of the substance stored inside can be prevented regardless of either of the surfaces face downward when the cartridge is placed.

Figure 2B:
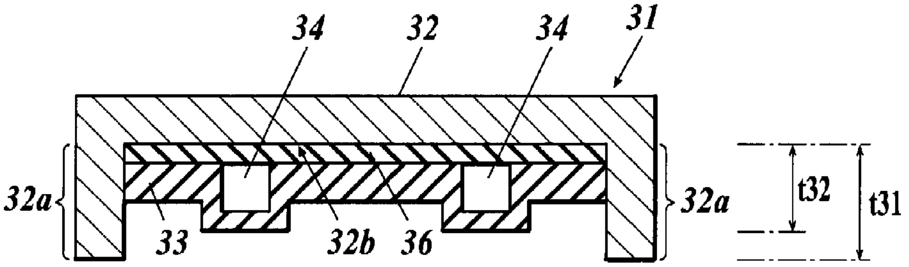
FIG. 2B is a cross sectional view of another example of the chemical reaction cartridge which the present invention is implemented.

FIG. 2B shows an example of the cartridge in which the flow path and the chambers are enclosed by the elastic body.

As shown in FIG. 2B, the substrate 32 of the chemical reaction cartridge 31 comprises the convex portions 32*a* which protrude further than the elastic body 33 in the surface side at the surface 32*b* of the substrate 32 on which the elastic body 33 and 36 are formed. That is, the surface 32*b* being the baseline, the height t31 of the convex portions 32*a* is higher than the height t32 of the elastic body 33. The convex portions 32*a* are portions of the substrate 32 and are rigid bodies.

Similarly in the cases of the cartridge 1 and 11, the unexpected leakage or the flowing of the substance stored inside is also prevented in the cartridge 31.

Figure 3A:
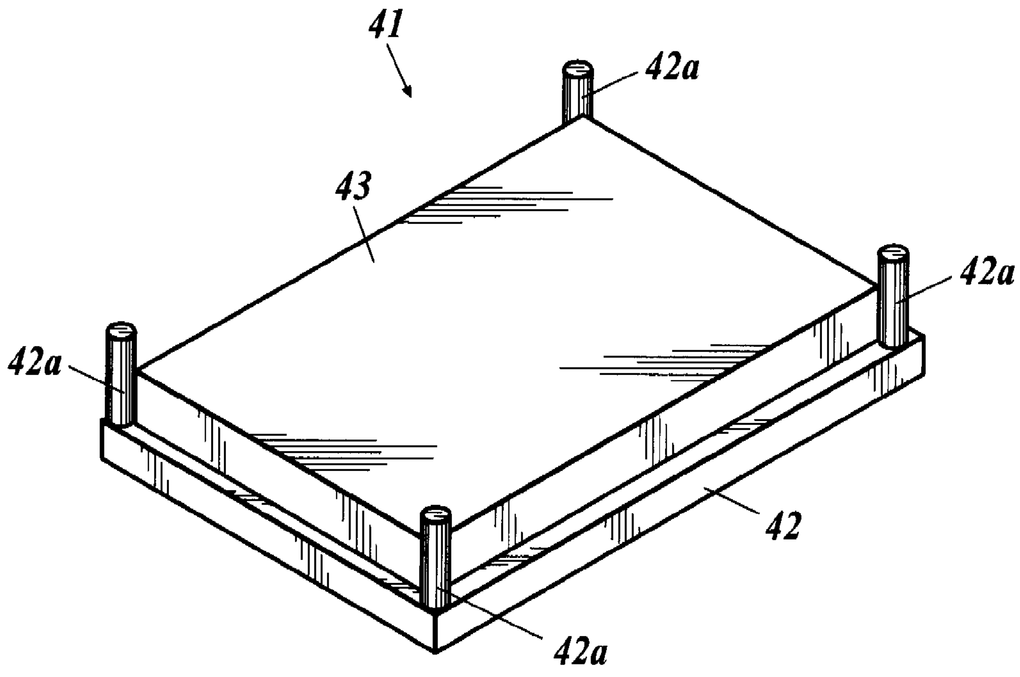
FIG. 3A is a perspective view of another example of the chemical reaction cartridge in which the present invention is implemented.
Figure 3B:
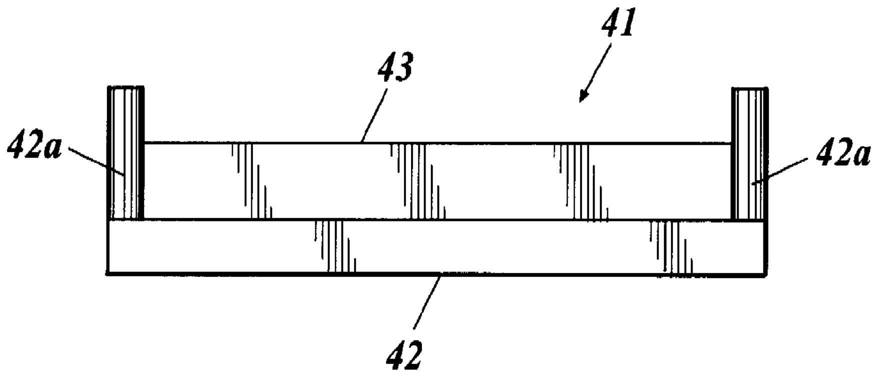
FIG. 3B is a front view of another example of the chemical reaction cartridge in which the present invention is implemented.

The above convex portions of the substrate may be formed so as to stand vertically at four corners of the substrate 42 as in the chemical reaction cartridge 41 shown in FIG. 3A. As shown in FIG. 3A, the convex portions 42*a*, 42*a*, 42*a* and 42*a* are disposed at four corners of the substrate 42. In FIG. 3A, the reference numeral 43 is an elastic body.

Figure 4:
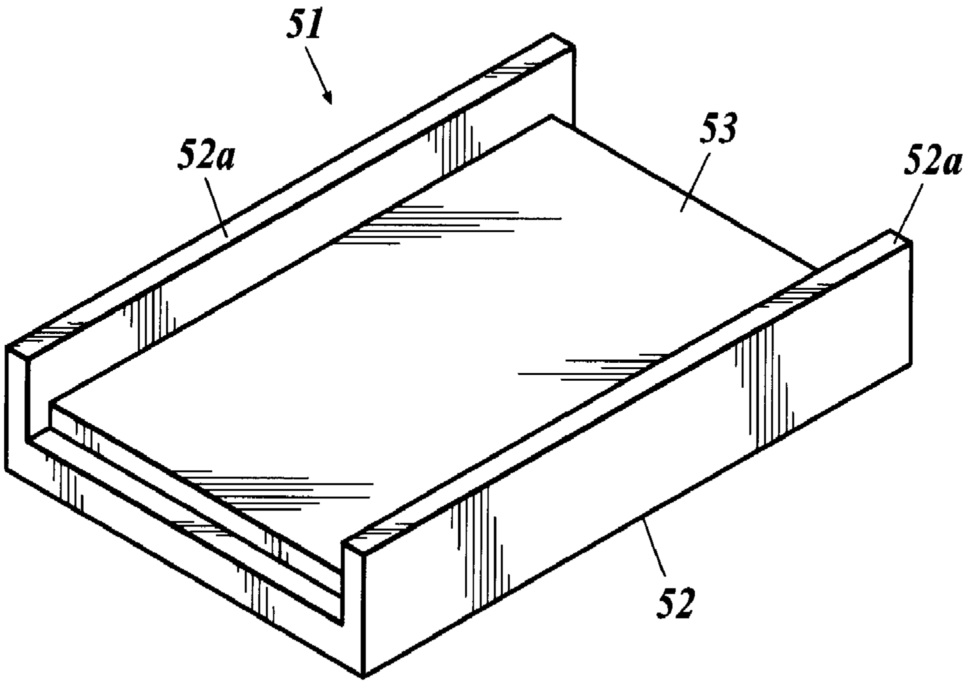
FIG. 4 is a perspective view of another example of the chemical reaction cartridge in which the present invention is implemented.

Further, the convex portions of the substrate may be formed in a continuous wall form as in the chemical reaction cartridge 51 shown in FIG. 4. As shown in FIG. 4, the convex portions 52*a* and 52*a* are respectively disposed at the two edges of the substrate 52 which face one another. Further, the convex portions 52*a* and 52*a* are formed in a long wall form along the edges. Among the two convex portions 52*a* and 52*a*, only one may be formed in a wall form and the other may be formed in a pin shape (column shape). In such case, the cartridge will be stably supported with more than three points by the convex portions of the substrate, and the same effect can be obtained. In FIG. 4, the reference numeral 53 is an elastic body.

As described above, the convex portions of the substrate are preferably disposed at the edges of the substrate. When the convex portions are disposed in the center portion of the substrate, the convex portions can easily become obstacles for the pressing by the roller or the like, and it will be difficult to use a roller or the like in a large size. When the convex portions of the substrate are disposed at the edges of the substrate, the roller 6 having the length w2 which is shorter than the size w1 which is the size between the convex portions 12*a* and 12*a* which are disposed at the edges facing one another can be applied as shown in FIG. 1B, and the entire surface of the elastic body can be pressed.

The convex portion of the substrate has the effect of preventing the unexpected pressing of the elastic body when the cartridge is placed by the elastic body directing downward even when there is one convex portion of the substrate and when the convex portion is in a pin shape (column shape).

However, in order to increase the sureness of the preventing effect and the stability of the cartridge at the time of placement, it is preferred to select the shape and the disposition of the convex portions of the substrate so that the supporting points by the convex portions of the substrate are more than three points and are not in straight line. For this purpose, a combination of more than three convex portions having a pin shape (column shape) or a combination of a wall formed convex portion and one pin shaped (column shaped) convex portion may be applied. It is preferred that the convex portions are not disposed in a straight line.

Figure 5:
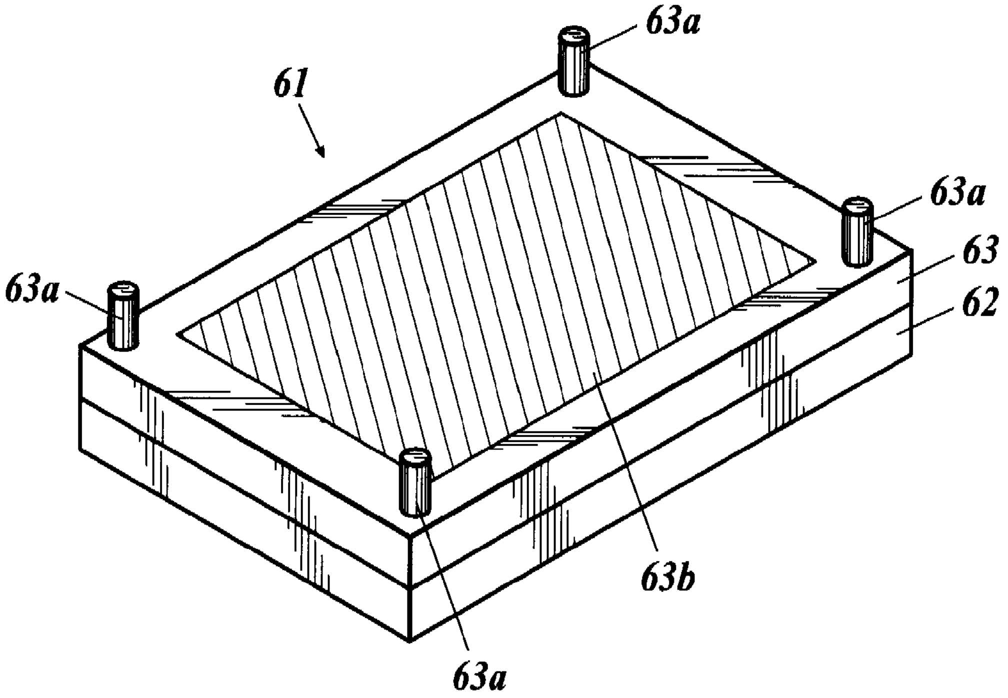
FIG. 5 is a perspective view of another example of the chemical reaction cartridge in which the present invention is implemented.

Moreover, it is effective to form the convex portions with an elastic body as shown in FIG. 5. The true intention of the object of preventing the unexpected pressing of the elastic body is to prevent the deformation of the flow path or the chambers. Therefore, the convex portions may be formed with an elastic body as in the chemical reaction cartridge 61 shown in FIG. 5. As shown in FIG. 5, the chemical reaction cartridge 61 comprises the substrate 62 and the elastic body 63, and four convex portions 63*a*, 63*a*, 63*a* and 63*a* are formed with the elastic body 63 at the periphery of the portion 63*b* in which the flow path or the chambers are formed. The convex portions 63*a* are disposed at the four corners of the cartridge 61. The convex portions 63*a* are protruded forward than the portion 63*b* in which the flow path or the chambers are formed. The flow path and the chambers are not formed outside the portion 63*b*.

According to the cartridge 61, the cartridge will be supported by the convex portions 63*a* of the elastic body even when the cartridge is placed by the surface on which the elastic body is formed directing downward. Therefore, the elastic body of the portion 63*b* in which the flow path or the chambers are formed is not pressed by the placing surface, and the flow path and the chambers are difficult to be deformed. Thus, there is an effect of preventing the unexpected leakage or flowing of the substance stored inside.

According to a first aspect of the preferred embodiments of the present invention, there is provided a chemical reaction cartridge comprising a substrate which is a rigid body and an elastic body, and a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the substrate includes convex portions which protrude further than the elastic body at a surface of the substrate, on which the elastic body is formed.

Preferably, the substrate includes not less than three convex portions to be used for supporting the cartridge, which are not arranged in one straight line when the cartridge is placed so as to direct a protruding direction of the convex portions downward.

Preferably, the convex portions are disposed at edges of the substrate.

Preferably, the convex portions are respectively disposed at the two edges of the substrate, which face one another.

Preferably, at least one edge of the two edges the convex portion has a long wall form along the one edge.

Preferably, the convex portions are respectively disposed at four corners of the substrate.

Preferably, the elastic bodies are formed on both sides of the substrate, and the convex portions are provided on both sides of the substrate.

Preferably, a specific portion constructed by the elastic body above the flow path or the chamber is protruded further than a surrounding portion constructed by the elastic body, which surrounds the specific portion.

Preferably, the specific portion constructed by the elastic body above the flow path or the chamber is thinner than the surrounding portion constructed by the elastic body.

According to a second aspect of the preferred embodiments of the present invention, there is provided a chemical reaction cartridge comprising a substrate which is a rigid body and an elastic body, and a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the elastic body includes a convex portion which protrude further than a portion of the elastic body in which the flow path or the chambers are formed at a surface of the substrate, on which the elastic body is formed.

According to the present invention, the cartridge is supported by the convex portions even when the cartridge is placed by the surface on which the elastic body is formed directing downward. Therefore, the deformation of the chambers or the flow path due to the dynamic action of the placing surface is difficult to occur, and the cartridge can be handled by a user with ease. Further, the leakage or an unexpected flowing of the fluid such as liquid stored inside are prevented. Therefore, there is an effect that the safeness and the preservability of the cartridge are increased.

The entire disclosure of Japanese Patent Application No. 2007-007795 filed on Jan. 17, 2007 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A chemical reaction cartridge, comprising:

a substrate which is a rigid body; and an elastic body, wherein a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the substrate includes convex portions which protrude further than the elastic body at a surface of the substrate, on which the elastic body is formed.

2. The chemical reaction cartridge as claimed in claim 1, wherein the substrate includes not less than three convex portions to be used for supporting the cartridge, which are not arranged in one straight line when the cartridge is placed so as to direct a protruding direction of the convex portions downward.

3. The chemical reaction cartridge as claimed in claim 1, wherein the convex portions are disposed at edges of the substrate.

4. The chemical reaction cartridge as claimed in claim 1, wherein the convex portions are respectively disposed at the two edges of the substrate, which face one another.

5. The chemical reaction cartridge as claimed in claim 4, wherein at least one edge of the two edges the convex portion has a long wall form along the one edge.

6. The chemical reaction cartridge as claimed in claim 1, wherein the convex portions are respectively disposed at four corners of the substrate.

7. The chemical reaction cartridge as claimed in claim 1, wherein the elastic bodies are formed on both sides of the substrate, and the convex portions are provided on both sides of the substrate.

8. The chemical reaction cartridge as claimed in claim 1, wherein a specific portion constructed by the elastic body above the flow path or the chamber is protruded further than a surrounding portion constructed by the elastic body, which surrounds the specific portion.

9. The chemical reaction cartridge as claimed in claim 8, wherein the specific portion constructed by the elastic body above the flow path or the chamber is thinner than the surrounding portion constructed by the elastic body.

10. A chemical reaction cartridge, comprising:

a substrate which is a rigid body; and an elastic body, wherein a flow path and two or more chambers connected by the flow path are formed inside the cartridge, the cartridge is structured so as to move or block a fluid substance in the flow path or the chamber by partially sealing the flow path, the chamber or the both of the flow path and the chamber by applying external force to the elastic body from outside, and the elastic body includes a convex portion which protrudes further than a portion of the elastic body in which the flow path or the chambers are formed at a surface of the substrate, on which the elastic body is formed, and the convex portion is formed at a portion of the elastic body in which the flow path or the chambers are not formed.

11. The cartridge of claim 10, wherein the elastic body includes plural convex portions, each of said plural convex portions disposed at a portion of the elastic body where the elastic body includes no flow path and no chamber.

* * * * *